(12) United States Patent
Shinoda

(10) Patent No.: US 7,782,512 B2
(45) Date of Patent: Aug. 24, 2010

(54) LIGHT IRRADIATION DEVICE, FINE PARTICLE ANALYZING APPARATUS, AND LIGHT IRRADIATION METHOD

(75) Inventor: Masataka Shinoda, Tokyo (JP)

(73) Assignee: Sony Corporation, Tokyo (JP)

( * ) Notice: Subject to any disclaimer, the term of this patent is extended or adjusted under 35 U.S.C. 154(b) by 197 days.

(21) Appl. No.: 12/185,613

(22) Filed: Aug. 4, 2008

(65) Prior Publication Data
US 2009/0057569 A1  Mar. 5, 2009

(30) Foreign Application Priority Data
Sep. 4, 2007  (JP) .............................. 2007-228782

(51) Int. Cl.
G02B 26/10  (2006.01)
G02B 26/08  (2006.01)
A61N 5/00   (2006.01)

(52) U.S. Cl. .............. 359/196.1; 359/201.1; 359/223.1; 250/492.1

(58) Field of Classification Search .............. 359/196.1, 359/198.1, 201.2, 202.1, 212.1, 212.2, 213.1, 359/214.1, 220.1, 221.1, 221.2, 223.1, 224.1, 359/226.1, 226.233–261; 250/492.1
See application file for complete search history.

(56) References Cited

U.S. PATENT DOCUMENTS

| | | | | |
|---|---|---|---|---|
| 3,710,279 A * | 1/1973 | Ashkin | ...................... | 250/281 |
| 3,808,550 A * | 4/1974 | Ashkin | ........................ | 372/97 |
| 5,852,493 A * | 12/1998 | Monnin | .................... | 356/141.1 |
| 6,242,754 B1 * | 6/2001 | Shiraishi | ..................... | 250/548 |
| 6,597,438 B1 | 7/2003 | Cabuz et al. | | |
| 7,149,017 B2 * | 12/2006 | Kandori et al. | .......... | 359/202.1 |
| 7,242,506 B2 * | 7/2007 | Kandori et al. | .......... | 359/196.1 |
| 7,344,273 B2 * | 3/2008 | Lewis et al. | .................. | 362/233 |
| 2004/0223135 A1 | 11/2004 | Ortyn et al. | | |
| 2005/0128546 A1 * | 6/2005 | Kandori et al. | ............. | 359/196 |
| 2006/0257089 A1 | 11/2006 | Mueth et al. | | |
| 2007/0103752 A1 * | 5/2007 | Kandori et al. | ............. | 359/196 |
| 2008/0035865 A1 * | 2/2008 | Komori et al. | .......... | 250/504 R |
| 2009/0059223 A1 * | 3/2009 | Shinoda | ..................... | 356/326 |
| 2009/0109436 A1 * | 4/2009 | Shinoda | ..................... | 356/337 |
| 2010/0019173 A1 * | 1/2010 | Someya et al. | ........... | 250/496.1 |

FOREIGN PATENT DOCUMENTS

DE  37 05 876  5/1993

(Continued)

OTHER PUBLICATIONS

"Cell Technology Supplementary Volume: Experiment Protocol Series, Flow Cytometry With Flexibility," by Hiromitsu Nakauchi, published in Aug. 31, 2006 by Shujunsha Co. Ltd., Second Edition, pp. 12 to 14.

(Continued)

*Primary Examiner*—Bernard E Souw
(74) *Attorney, Agent, or Firm*—K&L Gates LLP

(57) ABSTRACT

A light irradiation device irradiates a specimen in a flow channel with directional light. The light irradiation device includes a light source that emits the directional light, and an irradiation control unit that irradiates the specimen in the flow channel with light, obtains positional information of the specimen, and controls the irradiation of the directional light based on the positional information.

9 Claims, 4 Drawing Sheets

FOREIGN PATENT DOCUMENTS

| | | |
|---|---|---|
| EP | 0 543 514 | 5/1993 |
| JP | 01-270644 | 10/1989 |
| JP | 03-164848 | 7/1991 |
| JP | 05-296914 | 12/1993 |
| JP | 07-092076 | 7/1995 |
| JP | 11-037974 | 12/1999 |
| JP | 2004505272 | 2/2004 |
| JP | 2007-046947 | 2/2007 |
| JP | 2007-057338 | 8/2007 |
| JP | 2008536129 | 9/2008 |
| JP | 05-142137 | 10/2009 |
| WO | 2006110749 | 10/2006 |
| WO | 2006/115663 | 11/2006 |
| WO | 2007/018087 | 2/2007 |

OTHER PUBLICATIONS

"Cell Technology Supplementary Volume: Experiment Protocol Series, Flow Cytometry With Flexibility," by Hiromitsu Nakauchi, Published in Aug. 31, 2006 by Shujunsha Co. Ltd., Second Edition, pp. 12 to 13.

Japanese Office Action issued on Sep. 8, 2009, for corresponding Japanese Patent Application JP007-228782.

* cited by examiner

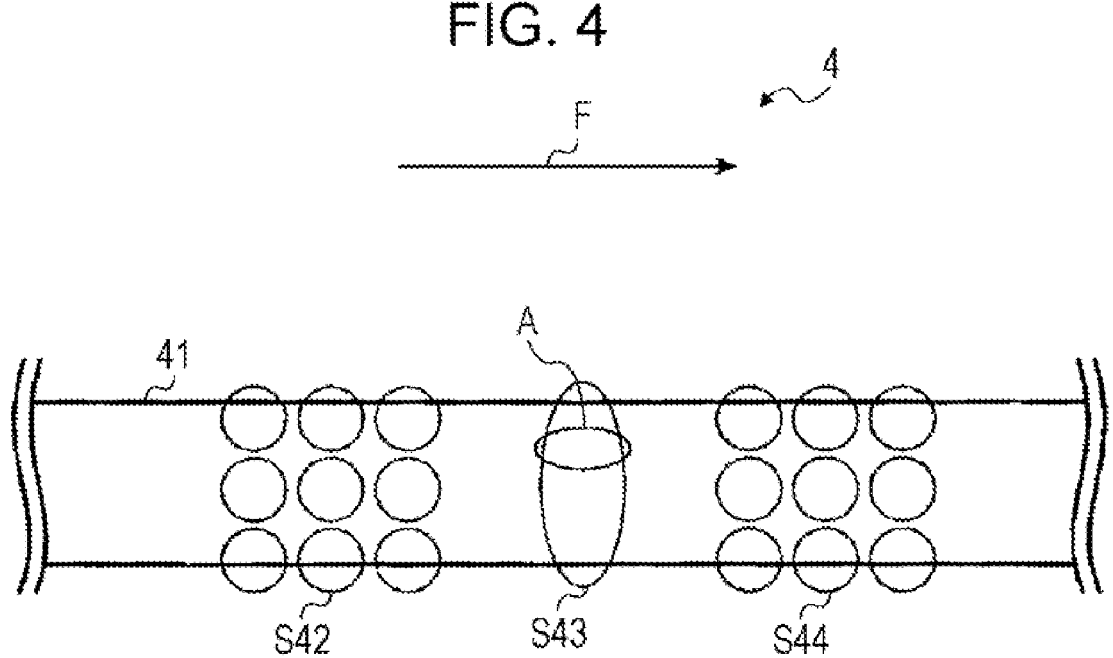
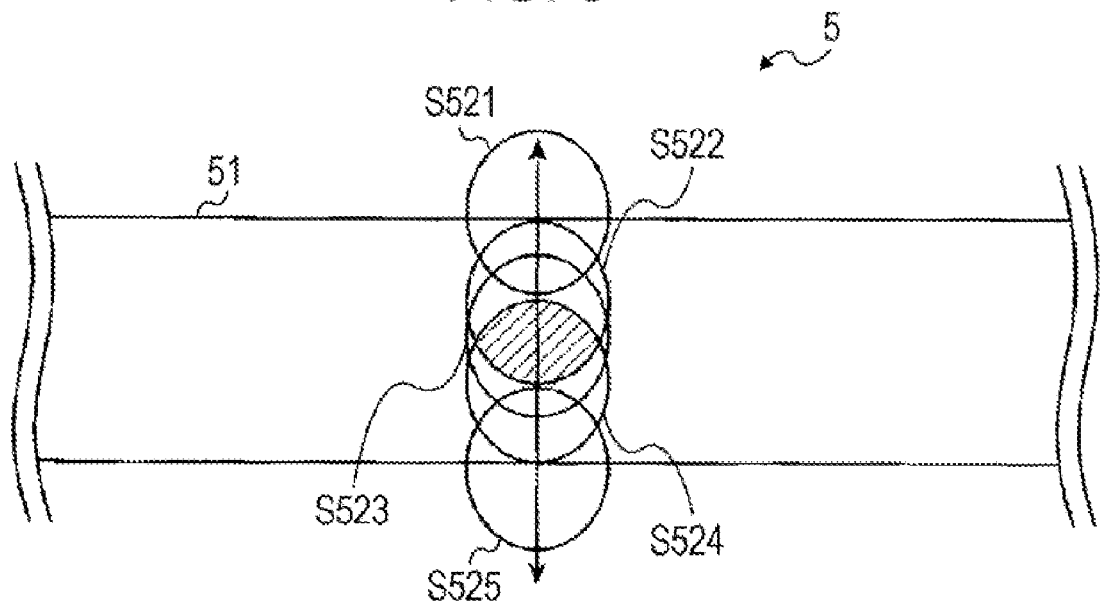

LIGHT IRRADIATION DEVICE, FINE PARTICLE ANALYZING APPARATUS, AND LIGHT IRRADIATION METHOD

CROSS REFERENCES TO RELATED APPLICATIONS

The present application claims priority to Japanese Patent Application JP 2007-228782 filed in the Japanese Patent Office on Sep. 4, 2007, the entire contents of which is incorporated herein by reference.

BACKGROUND

The present application relates to a light irradiation device, a fine particle analyzing apparatus, and a light irradiation method. In particular, the present application relates to a technique of irradiating a specimen in a flow channel with light.

An irradiation technique with directional light such as laser light is widely used for spectrometry, processing technology, and the like. Directional light has a single wavelength and an aligned phase. When the directional light is converged with a lens or the like, the light can be condensed at a small point. Thus, the directional light has a characteristic that an irradiation point has a high energy density.

Laser spectroscopy may be classified into linear laser spectroscopy, non-linear spectroscopy, and the like. The linear laser spectroscopy for measurement of an absorption spectrum or an excitation spectrum has high sensitivity and resolution in comparison with spectroscopy which uses an existing light source. The non-linear laser spectroscopy can provide spectrum with further high sensitivity and resolution. For example, the non-linear laser spectroscopy includes laser induced fluorescence spectroscopy, laser Raman spectroscopy, coherent anti-Strokes Raman scattering (CARS), polarization spectroscopy, resonance ionization spectroscopy, photoacoustic spectroscopy, and the like. A configuration particularly having a high time resolution provides picosecond spectroscopy or femtosecond spectroscopy.

For example, laser irradiation technology is used in flow cytometry (refer to "Cell Technology Supplementary Volume: Experiment Protocol Series, Flow Cytometry With Flexibility," by Hiromitsu Nakauchi, Published in Aug. 31, 2006 by Shujunsha Co. Ltd., Second Edition, pp. 12 to 13). Flow cytometry is a measurement method in which living cells as a measurement subject are sorted and, for example, the function of the cells is analyzed. Cells are fed into a laminar flow, and the cells passing through the flow cells are irradiated with laser light. The irradiation causes fluorescent light or scattered light to be generated, and the light is measured. A pulse detection system detects the fluorescent light or scattered light, which is generated when the cells pass through an irradiation spot with the laser light, as an electric pulse. The pulse detection system analyzes the cells through analysis of a pulse height, a pulse width, a pulse area of the electric pulse. With the detection of fluorescent light or scattered light emitted from individual cells, the characteristics of living cells can be analyzed.

SUMMARY

However, when irradiation with directional light such as laser light has to be provided continuously or for a long time, the life or operation time of a light source of the laser light or the like is restricted. Also, when a specimen in a flow channel is irradiated with directional light, irradiation unevenness, irradiation deviation, or defocus, may be generated depending on relationship between the position of the specimen in the flow channel and the position of an irradiation spot with the laser light.

Accordingly, it is desirable to provide a light irradiation device capable of preventing the irradiation unevenness, irradiation deviation, or defocus from being generated according to an embodiment.

A light irradiation device that irradiates a specimen in a flow channel with directional light is provided according to an embodiment. The light irradiation device includes at least a light source that emits the directional light, and an irradiation control unit that irradiates the specimen in the flow channel with light, obtains positional information of the specimen, and controls the irradiation of the directional light based on the positional information.

Since the positional information of the specimen in the flow channel is obtained in advance, the directional light can be emitted at a further precise position or depth. Accordingly, the irradiation can be precisely provided for the specimen in the flow channel without continuous or long-time irradiation. Also, the irradiation unevenness, irradiation deviation, and defocus can be reduced.

In this embodiment, an irradiation target position of the light for obtaining the positional information may be preferably a position in the flow channel located upstream of an irradiation target position of the directional light. Also, the light for obtaining the positional information may be preferably emitted at a plurality of positions in the flow channel. Accordingly, further precise positional information can be obtained.

In an embodiment, the light for obtaining the positional information may be preferably obtained by dividing the emitted directional light. Since the directional light is divided, the necessary number of light sources can be reduced. Accordingly, the configuration of the light irradiation device can be simplified.

In addition, a fine particle analyzing apparatus is provided according to another embodiment. The fine particle analyzing apparatus includes a light irradiation portion, which has a light source that emits directional light and an irradiation control unit that irradiates fine particles in a flow channel with light, obtains positional information of the fine particles, and controls the irradiation of the directional light based on the positional information. Since the position of the specimen in the flow channel is obtained in advance, the irradiation unevenness, irradiation deviation, and defocus of the directional light can be reduced. Accordingly, the fine particle analyzing apparatus can provide further highly precise analysis.

In an embodiment, the fine particle analyzing apparatus may preferably further include at least one of a processing portion that processes the fine particles in the flow channel based on the positional information, a treating portion that treats the fine particles in the flow channel based on the positional information, and a sorting portion that sorts the fine particles in the flow channel based on the positional information. Hence, the position information can be reflected to not only the light irradiation with the light irradiation portion, but also the process of processing, treating, or sorting. Accordingly, the process of processing, treating, or sorting can be performed highly precisely.

Here, the "processing" means addition of any king of processing to a specimen. The processing includes mechanical processing and artificial processing. The "treating" means addition of any kind of treatment to a specimen. The "sorting" means sorting of specimens in accordance with a certain standard.

Further, a light irradiation method of irradiating a specimen in a flow channel with directional light is provided according to still another embodiment. The method includes at least the steps of irradiating the specimen in the flow channel with light and obtaining positional information of the specimen, and irradiating the specimen with the directional light based on the positional information.

With this embodiment, since the positional information of the specimen in the flow channel is obtained, the directional light can be emitted at a proper position.

Additional features and advantages are described herein, and will be apparent from the following Detailed Description and the figures.

BRIEF DESCRIPTION OF THE FIGURES

FIG. 4 is an illustration briefly showing a light irradiation device according to a fourth embodiment;

FIG. 5 is an illustration briefly showing a light irradiation device according to a fifth embodiment.

DETAILED DESCRIPTION

Hereinafter, light irradiation devices are described below according to an embodiment with reference to the attached drawings. It is noted that the embodiments shown in the attached drawings are merely examples according to typical embodiments, which do not intend to limit the scope of the present application.

Figure 1:
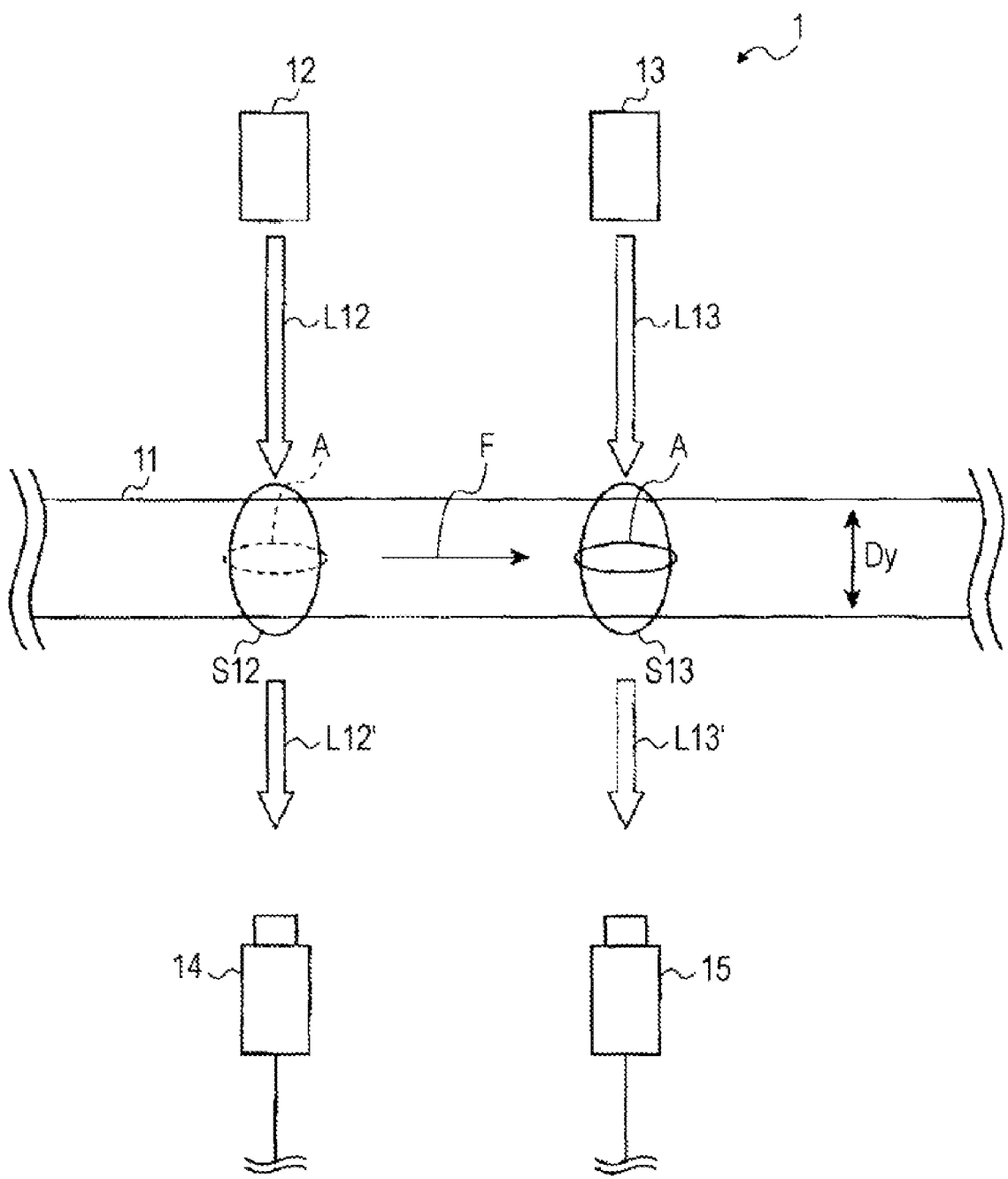
FIG. 1 is an illustration briefly showing a light irradiation device according to a first embodiment.

FIG. 1 is an illustration briefly showing a light irradiation device according to a first embodiment.

In FIG. 1, a light irradiation device 1 is illustrated. The size and arrangement of the light irradiation device 1 may be selected in accordance with the purpose of use. The configuration of the light irradiation device 1 may be designed or modified in a suitable manner according to an embodiment.

The light irradiation device 1 includes at least a flow channel 11 in which a specimen A is present, and light sources 12 and 13. The light source 12 emits light L12 for irradiation to obtain positional information of a specimen A. The light source 12 is used as an irradiation control unit for the light source 13. The light source 13 emits directional light L13.

Directional light emitted from the light source 13 is not particularly limited. For example, directional light of a laser or a light emission diode (LED) may be used.

For example, when a laser is used, the type of the laser is not limited. A laser suitable for the purpose of use may be selected. The purpose of use may be analyzing, measuring, heating, or processing. A medium suitable for the purpose of use may be selected. For example, the medium may be a semiconductor laser, a liquid laser, a gas laser, or a solid-state laser.

The semiconductor laser may be a GaAs laser, or an InGaAsP laser. The gas laser may be a He—Ne laser (red), an Ar laser (visible, blue or green), a $CO_2$ laser (infrared), or an excimer laser (violet or other color). The liquid laser may be a dye laser. The solid-state laser may be a ruby laser, a YAG laser, or glass laser. Also, a diode pumped solid-state laser (DPSS) may be used. The DPSS excites a solid-state medium such as a Nd:YAG by a laser diode (LD) for oscillation.

The specimen A flows in a direction indicated by arrow F in the flow channel 11. The light source 12 irradiates the specimen A with the light L12. An irradiation position of the light L12 corresponds to a position of an irradiation spot S12. When the specimen A is irradiated with the light L12, measurement subject light L12' is generated. A detector 14 measures the measurement subject light L12'. Accordingly, the positional information of the specimen A can be obtained.

An analogue-to-digital converter (ADC) or the like converts measurement data of the measurement subject light L12' into a digital signal, and a computer arithmetically processes the signal. Though not shown, the processed signal can be fed back to the detector 14, as information for controlling irradiation of the light source 13.

The type of the measurement subject light L12' is not limited. A suitable detection method may be employed with regard to the type of specimen A, a measurement condition, and the like. The measurement subject light L12' may be fluorescent light or scattered light generated from the specimen A. An example of the detection method may be that the specimen A is labeled with a specific fluorescent material in advance, the light source 12 irradiates the specimen A with exciting light as the light L12, and fluorescent light generated as a result of the irradiation is detected as the measurement subject light L12'.

When a fluorescent dye is used, a fluorescent dye corresponding to a wavelength of the light L12 (for example, a wavelength of a laser) may be used. For example, when an Ar ion laser (488 nm) is used, a fluorescent dye, such as fluorescein isothiocyanate (FITC), phycoerythrin (PE), or peridinin chlorophyll protein (PerCP), may be used. When a He—Ne laser (633 nm) is used, a fluorescent dye, such as allophycocyanin (APC), or APC-Cy7, may be used. When a dye laser (598 nm) is used, a fluorescent dye such as Texas Red (TR) may be used. When a Cr laser (407 nm) or a semiconductor laser is used, a fluorescent dye such as Cascade Blue may be used.

Another example of the detection method using the measurement subject light L12' may be that labeling or the like is not performed, and scattered light from the specimen A is detected. For example, scattered light generated when the laser light passes through the specimen A may be detected.

Based on the obtained positional information, the subsequent light source 13 emits the directional light L13 toward an irradiation spot S13. An irradiation condition is controlled by the irradiation control unit based on the obtained positional information.

When the specimen A moves in the flow channel 11 (see arrow F in FIG. 1), irradiation unevenness may be generated as a result of the irradiation with the directional light L13 depending on the speed at which the specimen A moves in the flow channel 11 or the position of the specimen A. In the past, the specimen A has been detected and measured only during a time in which the specimen A passes through the irradiation spot with the directional light. Hence, it is difficult to obtain detailed positional information. Thus, the specimen A may be insufficiently irradiated with the directional light L13, irradiation for a long time has to be performed, and an irradiation spot diameter has to be increased.

In particular, when the size of a specimen A is smaller than a flow channel width of the flow channel 11, the specimen A moves in the flow channel 11 with a certain degree of freedom. This may cause irradiation unevenness, irradiation deviation, or defocus, depending on a beam diameter of the irradiation spot S13 with the directional light L13. Such defective irradiation may be a factor of deterioration in irradiation efficiency of the directional light L13. In addition, the irradiation with the directional light L13 has to be continuously performed to overcome the above problems. Hence, the life of the light source 13 is reduced, and the operation time thereof is restricted.

In contrast, the positional information of the specimen A is detected in advance at a position located upstream of the irradiation spot S13, by the irradiation control unit. Hence, the moving speed, position, and laminar flow width of the specimen A in the flow channel 11 can be obtained. The irradiation control unit may adjust, for example, the irradiation power, irradiation time, and irradiation position, based on the positional information.

The positional information of the specimen A represents information relevant to the flow rate and three-dimensional position of the specimen A in the flow channel 11. The positional information contains various information relevant to vectors of the specimen A in the flow channel 11.

In an embodiment, with the positional information of the specimen A in the flow channel 11, the irradiation power, irradiation time, and irradiation position of the directional light L13 can be adjusted or optimized. As a result, the irradiation unevenness, irradiation deviation, defocus, and the like, can be reduced. Also, with the positional information, a time in which the specimen A moves from the irradiation spot S12 to the irradiation spot S13 can be predicted.

Accordingly, in an embodiment, a control can be provided so that the specimen A is irradiated with the directional light L13 when the specimen A reaches the irradiation spot S13. With this control, the light source 13 does not have to continuously emit the directional light L13. This can make a contribution to increase in the life of the light source, and reduction in a load to the light irradiation device.

For example, a time at which the specimen A reaches the irradiation spot S13 may be predicted to determine a timing at which the specimen A is irradiated with the directional light L2, based on the time in which the specimen A moves from the irradiation spot S12 to the irradiation spot S13. The irradiation with the directional light L13 does not have to be continuously performed. The life of the light source 13 can be further increased. Also, positional information containing a depth (Z direction) of the specimen, and a moving speed of the specimen may be detected. Accordingly, the detected data can be reflected to a process for processing, treating, or sorting the specimen, the process being performed separately. That is, the detected data can be used as a trigger timing for the process.

The light irradiation device 1 according to an embodiment, if necessary, may detect light as measurement light L13', which is generated when the light source 13 irradiates the specimen A with light. In this case, the light irradiation device 1 may be used as, for example, a spectrometric instrument. In particular, a light-receiving portion 15 corresponding to the light source 13 may be provided. In this case, fluorescent light or scattered light may be detected as measurement light, as described above.

In an embodiment, the type of specimen A in the flow channel 11 is not limited. For example, the specimen A can be precisely irradiated even when the specimen A is a fine particle or a structure, such as a cell or a bead. A medium provided in the flow channel 11 may be any solution or gas as long as the medium is fluid. The medium may be properly selected with regard to the type of specimen A, irradiation condition, and the like.

Also, the configuration to which the positional information is reflected is not limited to an optical system for the light irradiation. For example, a flow-rate control unit may be provided. The flow-rate control unit controls the flow rate of the medium in the flow channel 11 based on the positional information (in particular, moving speed etc.) of the specimen. With the adjustment of the flow rate of the medium in the flow channel 11 based on the positional information, the directional light L13 can be emitted at a further precise position of the specimen A.

Further, a positioning unit may be provided. The positioning unit positions the specimen A as an irradiation subject in the irradiation spot S13 with the directional light L13 based on the positional information. A timing at which the specimen A is fed to the irradiation spot S13 may be expected, so that the specimen A is positioned at a proper timing only for a predetermined period. With the positioning unit, the directional light L13 can be emitted at a further precise position. A unit for adjusting the flow rate and a unit for positioning are not limited to the above-described units. For example, the flow rate may be directly adjusted, or the flow channel may be made of elastic resin or the like and the flow channel width may be deformed by pressing or the like.

The spot diameter of the irradiation spot S12 with the light L12 is not limited. Preferably, the spot diameter may be smaller than a flow channel width Dy of the flow channel 11. Since the spot diameter is smaller than the flow channel width Dy, further precise positional information can be obtained. The positional information provides the position of the specimen A in the flow channel width Dy direction.

The irradiation spot S12 with the light L12 for obtaining the positional information is preferably located immediately upstream of the irradiation spot S13 with the directional light L13. Since the positional information for the position located immediately upstream of the irradiation spot S13 is obtained, a proper irradiation target position of the irradiation spot S13 with the directional light L13 can be further precisely obtained.

Also, the spot form, spot size (for example, beam diameter), light quantity, energy profile, and the like, of the irradiation spot S13 with the directional light L13 are not particularly limited, and may be properly determined in accordance with the purpose of use.

Figure 2:
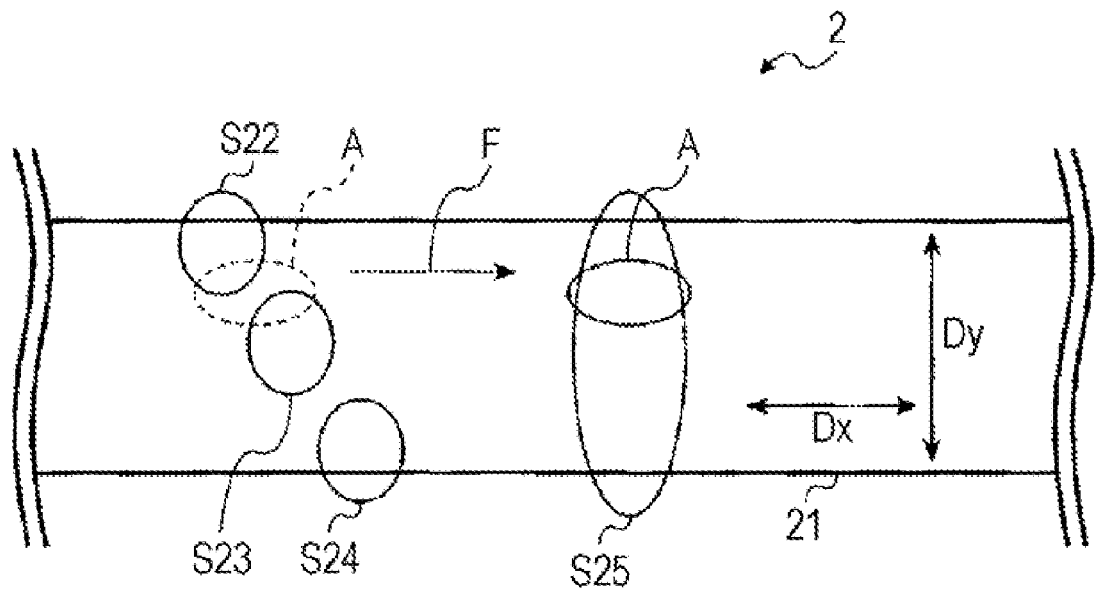
FIG. 2 is an illustration briefly showing a light irradiation device according to a second embodiment.

FIG. 2 is an illustration briefly showing a light irradiation device according to a second embodiment.

In FIG. 2, a light irradiation device 2 is illustrated. The light irradiation device 2 is different from that of the first embodiment for the light irradiation position to obtain positional information. Hereinafter, different points are mainly described while descriptions for common points to a first embodiment are omitted. FIG. 2 illustrates only the irradiation spot position of light irradiation, and omits other portions.

The light irradiation device 2 irradiates a specimen A in a flow channel 21 with light for obtaining positional information, the light being emitted on a plurality of irradiation spots S22, S23, and S24. Then, directional light is emitted on an irradiation spot S25 based on the obtained positional information.

Since the light for obtaining the positional information is emitted on the plurality of irradiation spots S22, S23, and S24, the detailed positional information of the specimen A can be detected.

For example, in FIG. 2, when the specimen A is located at a position so as to extend between the irradiation spots S22 and S23 (see a dotted-line region in FIG. 2), the positional information of the specimen A can be detected based on measurement subject light (not shown) obtained from the light emitted on the irradiation spot S22 and measurement subject light (not shown) obtained from the light emitted on the irradiation spot S23.

In order to more precisely obtain the position of the specimen A in a flow channel direction (Dx) and in the flow channel width direction (Dy) of the flow channel 21, a plurality of irradiation spots may be desirably provided at different positions in the flow channel direction and the flow channel width direction. In particular, referring to FIG. 2, the irradiation spot S23 is arranged downstream and downward of the irradiation spot S22, and the irradiation spot S24 is arranged downstream and downward of the irradiation spot S23. With this arrangement, time-lapse positional information of the specimen A can be obtained.

The detection is not limited to the detection of the two-dimensional positional information (Dx and Dy). When three-dimensional positional information is to be detected, focus positions of a plurality of irradiation spots may be adjusted and arranged. Accordingly, positional information in a depth direction (Z direction) can be detected.

The method of emitting the light for obtaining the positional information at the plurality of positions is not limited. A plurality of light sources may be provided respectively for the irradiation spots, a single light source may perform irradiation during scanning, or light emitted from a single light source may be divided.

When the single light source scans, the scanning is not limited to two-dimensional scanning, and may be three-dimensional scanning which contains scanning in the depth direction of the flow channel 21. A scanning unit is not particularly limited. An existing scanning unit may be used.

Though not shown, detectors may be provided respectively for the irradiation spots S22, S23, and S24. With the detectors, precise positional information of the specimen A can be obtained, based on measurement data obtained by the detectors.

Figure 3:
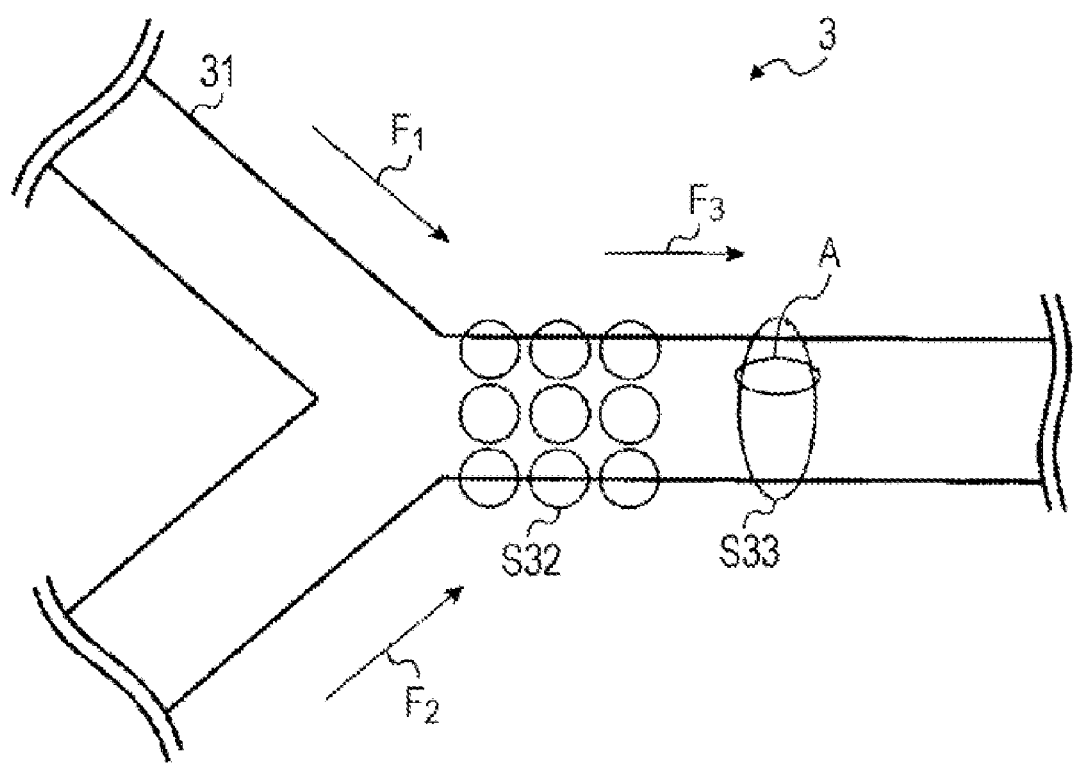
FIG. 3 is an illustration briefly showing a light irradiation device according to a third embodiment.

FIG. 3 is an illustration briefly showing a light irradiation device according to a third embodiment.

In FIG. 3, a light irradiation device 3 is illustrated. The light irradiation device 3 is different from that of the first embodiment for the irradiation spot position of light irradiation to obtain positional information, the shape of a flow channel 31, and the like. Hereinafter, different points are mainly described while descriptions for common points to the first embodiment are omitted. FIG. 3 illustrates only the irradiation spot position of light irradiation, and omits other portions.

The light irradiation device 3 includes the flow channel 31 which has a structure split toward the upstream side of the irradiation position. A specimen A fed in a moving direction $F_1$ and a specimen A fed in a moving direction $F_2$ are joined, and then fed in a moving direction $F_3$ to the irradiation position.

The light irradiation device 3 irradiates the specimen A in the flow channel 31 with light for obtaining positional information, the light being emitted on nine irradiation spots S32. Then, directional light is emitted on an irradiation spot S33 based on the obtained positional information.

Since the light for obtaining the positional information is emitted on the plurality of irradiation spots S32 in the flow channel 31, detailed positional information of the specimen A can be detected. In the light irradiation device 3, the flow channel 31 is imaginary divided into regions arranged substantially in a grid form. The light for obtaining the positional information is emitted in each of the regions.

When the flow channel 31 is split, the specimen A is fed in the flow channel 31 in the moving direction $F_3$ with a rotational motion or other motion. In this case, the number of the irradiation spots S32 with the light for obtaining the positional information may be increased so as to cover a flow channel space in the flow channel 31. Accordingly, time-lapse positional information of the specimen A can be obtained. As a result, further precise positional information can be detected.

FIG. 4 is an illustration briefly showing a light irradiation device according to a fourth embodiment.

In FIG. 4, a light irradiation device 4 is illustrated. The light irradiation device 4 is different from that of a first embodiment in that irradiation spots as a result of light irradiation for obtaining positional information are located upstream and downstream of an irradiation spot with directional light. Hereinafter, different points are mainly described while descriptions for common points to the first embodiment are omitted. FIG. 4 illustrates only the irradiation spot position of light irradiation, and omits other portions.

The light irradiation device 4 irradiates the specimen A in a flow channel 41 with light for obtaining positional information, the light being emitted on irradiation spots S42. Then, directional light is emitted on an irradiation spot S43. Further, light for obtaining positional information is emitted on irradiation spots S44 located downstream of the irradiation spot S43. Since the light for obtaining the positional information is emitted on the irradiation spots S42 and S44, further precise positional information can be obtained.

In addition, since the light for obtaining the positional information is emitted on the irradiation spots S44 after the directional light is emitted on the irradiation spot S43, the position of the specimen A irradiated with the directional light in a region located downstream of the flow channel 41 can be obtained. Even when measurement subject light is not detected in the upstream irradiation spots S42, measurement subject light can be detected in the downstream irradiation spots S44. Accordingly, further precise positional information can be obtained. As described above, the positional information of the specimen A in the downstream region of the flow channel 41 can be reflected to the light irradiation of the directional light.

Though not shown, when the specimen A is sorted in the downstream region of the flow channel 41, the positional information can be reflected to obtain the position of the specimen in the flow channel 41 and the speed thereof toward an expected sorting position. This will be described later.

FIG. 5 is an illustration briefly showing a light irradiation device according to a fifth embodiment.

In FIG. 5, a light irradiation device 5 is illustrated. The light irradiation device 5 is different from that of the first embodiment and other embodiments in that light for obtaining positional information is emitted during scanning. Hereinafter, different points are mainly described while descriptions for common points to the first embodiment are omitted. FIG. 5 illustrates only the irradiation spot position of light irradiation, and omits other portions.

The light irradiation device 5 provides irradiation spots S521, S522, S523, S524, and S525 provided in a flow channel width direction of a flow channel 51, as irradiation spots for irradiation of a specimen A in the flow channel 51. The light irradiation on the irradiation spots is provided by a single light source which emits light during scanning (see an arrow in FIG. 5). The irradiation spots S521, S522, S523, S524, and S525 of the light irradiation during scanning may be irradiation spots with light for obtaining positional information, or irradiation spots with directional light.

Since the light for obtaining the positional information performs scanning, the number of light sources may be one. Hence, the configuration of the light irradiation device can be simplified. The light for obtaining the positional information may be preferably directional light. In particular, as a preferable light irradiation method for irradiating the specimen A in the flow channel 51 with the directional light, the directional light providing a smaller irradiation spot than a flow channel width of the flow channel 51 is emitted on the specimen A while scanning in the flow channel width direction of the flow channel 51.

Also, since the irradiation of the directional light is provided during scanning, areal power density of the irradiation spot can be relatively increased (see an oblique-line region in FIG. 5). As a result, original power of the light source can be reduced, laser condensing efficiency can be improved, and electric power consumption can be reduced.

A plurality of irradiation spots may be formed at desirable positions of the flow channel 51 through optical scanning. Hence, the positional information and the measurement subject light (fluorescent light or scattered light) can be detected through light irradiation scanning at a high speed in the flow channel 51 regardless of the position of the specimen A in the flow channel 51.

The scanning speed of the directional light is not limited to a constant speed, and may be varied with regard to the purpose of use, irradiation condition, and the like. However, scanning at a high speed is preferable. Accordingly, the light irradiation can be reliably provided for the specimen A which moves in the flow channel 51. Further, the light irradiation can be performed a plurality of times. More particularly, the light irradiation is preferably performed under the condition of Expression (1) as follows:

$$\frac{D_2}{v_1} > \frac{D_1}{v_2} \quad (1)$$

where $v_1$ is a moving speed of a specimen in a flow channel, $v_2$ is a scanning speed of directional light, $D_1$ is a flow channel width, and $D_2$ is an irradiation spot diameter.

The left side of Expression (1) is obtained such that "the irradiation spot diameter $D_2$" is divided by "the moving speed $v_1$ of the specimen A in the flow channel 51". This approximates a time in which the specimen A passes through the irradiation spot diameter. The irradiation spot diameter $D_2$ is not particularly limited, however, may be preferably in a range of from 1 to 100 µm. The moving speed $v_1$ of the specimen in the flow channel 51 is not particularly limited, however, may be preferably in a range of from 0.1 to 10 m/s.

The right side of Expression (1) is obtained such that "the flow channel width $D_1$" is divided by "the scanning speed $v_2$ of the directional light". This approximates a scanning time in which the directional light scans the flow channel width. The flow channel width $D_1$ is not particularly limited, however, may be preferably in a range of from 10 µm to 1 mm. The scanning speed $v_2$ of the directional light is not particularly limited, however, may be preferably in a range of from 1 to 50 m/s.

That is, the entire flow channel width is irradiated with light at least one time while the specimen A passes through the irradiation spot diameter. Hence, to increase the number of times of scanning, it is desirable that $(D_2/v_1)$ is sufficiently larger than $(D_1/v_2)$. In particular, it is desirable that $(D_2/v_1)$ is two to ten times larger than $(D_1/v_2)$. In this case, the scanning can be performed two to ten times while the specimen A passes through the irradiation spot (for example, the irradiation spot S523). Accordingly, efficiency of the directional light can be increased. By integrating detection signals through the plurality of times of the scanning, the signal/noise (S/N) ratio of the directional light can be further improved. For example, when a relatively dark subject such as fluorescent light is used, a fluorescent signal can be enhanced while a noise is reduced.

Also, when the flow channel width $D_1$ is decreased instead of the high-speed scanning, similar advantages can be obtained. Since the flow channel width $D_1$ is decreased, a scanning time for the irradiation spot (that is, $D_1/v_2$) can be reduced. With the scanning condition and flow channel structure, the specimen can be irradiated with the light a plurality of times. For example, when the light irradiation is performed N times, by integrating obtained signals, the S/N ratio of the detection signals can be further improved by $(N)^{1/2}$ times.

The scanning unit of the light irradiation is not particularly limited, however, scanning of the irradiation spot may be preferably performed by a galvanometer mirror, an electro-optical element, a polygonal mirror, a MEMS element, or the like. In particular, the electro-optical element is preferable because the electro-optical element does not have a movable portion, thereby being stable and reliable. A plurality of scanning units may be used.

Figure 6:
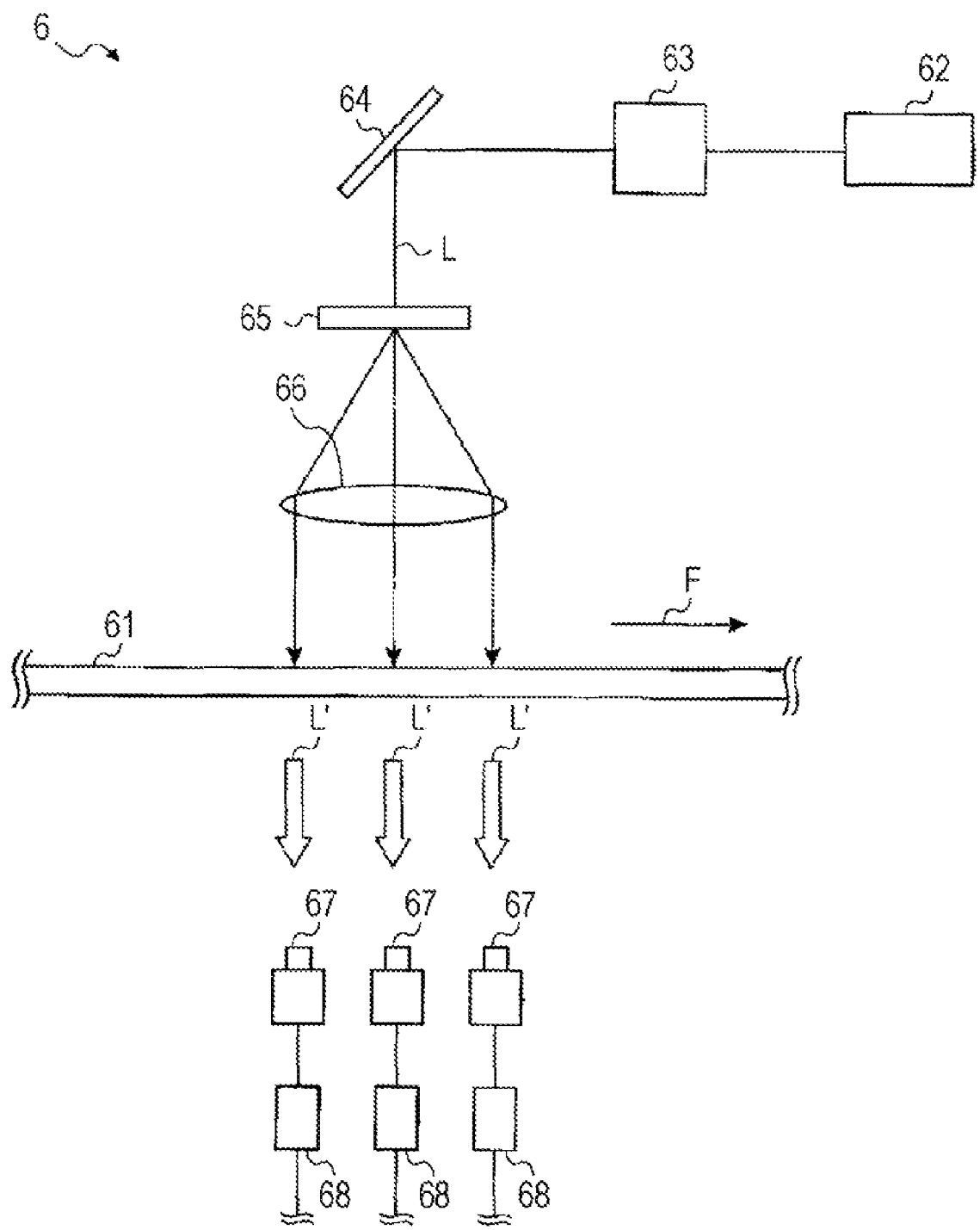
FIG. 6 is an illustration briefly showing a light irradiation device according to a sixth embodiment.

FIG. 6 is an illustration briefly showing a light irradiation device according to a sixth embodiment;

In FIG. 6, a light irradiation device 6 is illustrated. The light irradiation device 6 features that light for obtaining positional information and directional light are emitted from a single light source. Hereinafter, different points are mainly described while descriptions for common points to the first embodiment are omitted.

The light irradiation device 6 performs laser irradiation with laser light as directional light on a flow channel 61 in which a specimen A is present. The light irradiation device 6 includes a light source 62 that emits laser light L, a laser control unit 63, a mirror 64, a grating device 65, and an objective 66. Also, the light irradiation device 6 includes detectors 67 that detect measurement subject light L', and analogue-to-digital converters (ADCs) 68.

The light source 62 may be a laser oscillator, from which the laser light L is emitted. The laser control unit 63 may control the emitted laser light L to obtain a desirable irradiation power, irradiation wavelength, and irradiation spot. The laser control unit is not particularly limited, and may employ a proper method with regard to the purpose of use, type of directional light for irradiation, and the like.

For example, a convex lens or the like functioning as a beam expander may be used so as to adjust the beam diameter of the laser light L.

The laser light L is incident on the grating device 65 via the mirror 64. The laser light L is divided into three laser beams by the grating device 65, then the laser beams pass through the objective 66, and the laser beams are respectively emitted on irradiation spots (not shown) in the flow channel 61.

For example, the grating device may be a grating, a hologram, a MEMS element, a prism, or the like.

The type and structure of the grating is not limited as long as the grating can divide the laser light L into a plurality of laser beams. The grating may be a monochromator which utilizes a reflection grating or the like. The grating has advantages of increasing a dispersion as compared with the prism, and providing a good wavelength resolution.

The hologram is an element having a function which divides incident laser light into laser beams, and allows the laser beams to be incident on predetermined target positions.

For example, a condensing lens condenses the laser light L generated from the laser oscillator, and the hologram transmits the condensed laser light L. The hologram has an interference pattern corresponding to the target positions of the irradiation spots (not shown) to be irradiated with the condensed and then divided laser beams L. Accordingly, the laser light L can be divided into the plurality of laser beams.

The MEMS element may be, for example, a piezoelectric driven type MEMS element. In this case, the value of a voltage to be applied to the MEMS element is controlled. Accordingly, the laser light L can be oscillated so as to be emitted in a direction slightly inclined to the incidence direction of the laser light L by a predetermined angle. Such a MEMS element is provided between the light source and a diffraction optical element or the like (not shown), so that a diffraction pattern for each wavelength of incident light of laser L can be projected.

The laser light L divided into the three laser beams may be used in irradiation with light for obtaining positional information, and irradiation with main irradiation laser light. In particular, since the laser light from the single light source is divided into the laser beams, part of the laser beams can be used to detect the positional information. The number of divided laser beams is not limited to three, and may be any desirable number.

When laser irradiation is provided on the irradiation spots of the flow channel 61, measurement subject light L' is obtained. The detectors 67 detect the measurement subject light L'. The analogue-to-digital converters (ADCs) 68 convert measurement data obtained by the detectors 67 into digital signals. A CPU or the like (not shown) arithmetically processes the digital signals as positional information.

The obtained positional information is transmitted to the laser control unit 63. Accordingly, the positional information can be reflected to the irradiation power, irradiation time, and the like, of the laser. When processing, treating, or sorting of the specimen is performed as a separate process, the positional information can be reflected to the process, as a trigger signal.

As described above, since the single light source 62 is used to emit the plurality of beams of directional light, the configuration of an optical system can be further simplified, and the configuration of the entire light irradiation device can be simplified.

A light irradiation device may include a laser light source, emitting optical system that guides laser light emitted from the laser light source to irradiation spots, an optical detection system that detects measurement subject light generated from the irradiation spots, an arithmetically processing portion that arithmetically processes measurement data obtained from the optical detection system to obtain the processed data as positional information, and an irradiation control unit that controls irradiation of at least main laser light based on the positional information. At least the laser light may be divided into laser beams, so that the laser beams are emitted on irradiation spots.

As described above, since the positional information is fed back to the irradiation control unit, the main laser light can be emitted on a further precise position. Further, since the laser light emitted from the single light source is divided and emitted, the configuration of the light irradiation device can be simplified, and the number of light sources can be reduced, thereby saving the cost, and the maintenance of the light irradiation device can be facilitated.

A pattern of the irradiation spots in the light irradiation device 6 may employ any of the patterns of the irradiation spots according to the embodiments shown in FIGS. 1 to 5.

The pattern of the irradiation spots may be properly determined with regard to the purpose of use.

The light irradiation device and light irradiation method according to any of the embodiments may be applied to various technical fields. For example, these configurations may be applied to particle size distribution measurement, fluid image analysis, coordinate measurement, and measurement instruments and analyzers such as a laser microscope, which use directional light. In particular, these configurations may be applied to fine particle analyzing apparatuses and the like which measure fine particles as a measurement subject, utilizing a technique of irradiating a specimen in a flow channel with light.

The fine particle analyzing apparatuses may be analyzers, such as a flow cytometer, or a beads assay (flow-beads assay). That is, the configurations may be applied to a technique in which fine particles are irradiated with light, measurement subject light such as fluorescent light or scattered light is obtained as a result of the irradiation, and the particles are sorted.

Further, a fine particle analyzing apparatus according to an embodiment may further include a processing portion that processes a specimen in the flow channel based on the positional information. Alternatively or additionally, the fine particle analyzing apparatus may include a treating portion that treats a specimen in the flow channel based on the positional information. Still alternatively or additionally, the fine particle analyzing apparatus may include a sorting portion that sorts specimens in the flow channel based on the positional information.

With the embodiment, not only at least the processing portion, the treating portion, or the sorting portion is combined with the light irradiation device, but also the positional information of the specimen can be fed back to the portion. Accordingly, the process like processing, treating, or sorting can be precisely and efficiently performed.

The processing portion involves a configuration that adds any kind of processing to the specimen. For example, the processing includes machining, laser machining, surface treatment, and the like. The treating portion involves a configuration that adds any kind of treatment to the specimen. For example, the treatment includes chemical treatment, physical treatment, activation, heating, cleaning, and the like. The sorting portion involves a configuration that sorts the specimens in accordance with a certain standard. For example, the sorting includes separation of the specimens, sorting of the specimens, and the like.

For example, when the fine particle analyzing apparatus according to the embodiment is used for flow cytometry, the configuration may focus on measurement of the size, structure, and the like, of fine particles, or may sort the fine particles based on the measured size, structure, and the like of the fine particles. In particular, a configuration for sorting cells may be used as a cell sorter. With the cell sorter, several ten thousands to hundred thousand cells can be rapidly measured and sorted per second.

To sort fine particles, the light irradiation technique according to the embodiment may be used as an optical detection mechanism. That is, since laser irradiation can be provided at precise positions of fine particles (biological cells or the like) in a flow channel, the fine particles can be precisely and efficiently sorted even when the fine particles are, for example, stem cells which are present in biological cells by an extremely small number.

As described above, since proper laser irradiation can be provided for fine particles (cells, beads, or the like) in a flow channel while an unirradiation area is minimized, further highly precise detection can be performed. Further, the fine particle analyzing apparatus can provide real-time detection.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A light irradiation device that irradiates a specimen in a flow channel with a directional light, comprising:
    a light source that emits the directional light; and
    irradiation control means for irradiating the specimen in the flow channel with light, obtaining positional information of the specimen, and controlling the irradiation of the directional light based on the positional information.

2. The light irradiation device according to claim 1, wherein an irradiation target position of the light for obtaining the positional information is a position in the flow channel located upstream of an irradiation target position of the directional light.

3. The light irradiation device according to claim 1, wherein the light for obtaining the positional information is emitted at a plurality of positions in the flow channel.

4. The light irradiation device according to claim 1, wherein the light for obtaining the positional information is obtained by dividing the emitted directional light.

5. A fine particle analyzing apparatus comprising:
    a light irradiation portion, which includes
    a light source that emits directional light, and
    irradiation control means for irradiating fine particles in a flow channel with light, obtaining positional information of the fine particles, and controlling the irradiation of the directional light based on the positional information.

6. The fine particle analyzing apparatus according to claim 5, further comprising at least one of:
    a processing portion that processes the fine particles in the flow channel based on the positional information;
    a treating portion that treats the fine particles in the flow channel based on the positional information; and
    a sorting portion that sorts the fine particles in the flow channel based on the positional information.

7. A light irradiation method of irradiating a specimen in a flow channel with directional light, comprising:
    irradiating the specimen in the flow channel with light and obtaining positional information of the specimen; and
    irradiating the specimen with the directional light based on the positional information.

8. A light irradiation device that irradiates a specimen in a flow channel with directional light, comprising:
    a light source that emits the directional light; and
    an irradiation control unit that irradiates the specimen in the flow channel with light, obtains positional information of the specimen, and controls the irradiation of the directional light based on the positional information.

9. A fine particle analyzing apparatus comprising:
    a light irradiation portion, which includes
    a light source that emits directional light, and
    an irradiation control unit that irradiates fine particles in a flow channel with light, obtains positional information of the fine particles, and controls the irradiation of the directional light based on the positional information.

* * * * *